United States Patent [19]

Trauffer

[11] Patent Number: 5,508,012
[45] Date of Patent: Apr. 16, 1996

[54] METHODS FOR RECOVERING SODIUM SULFIDES FROM A SULFUR SCAVENGING REACTION

[75] Inventor: Edward A. Trauffer, Rydal, Pa.

[73] Assignee: Quaker Chemical Corporation, Wilmington, Del.

[21] Appl. No.: 277,395

[22] Filed: Jul. 19, 1994

Related U.S. Application Data

[63] Continuation-in-part of Ser. No. 26,891, Mar. 5, 1993, Pat. No. 5,347,003.

[51] Int. Cl.$^6$ ............................................... C07C 211/09
[52] U.S. Cl. .................................. 423/206.1; 423/206.2; 423/208; 423/225; 423/566.3; 423/638
[58] Field of Search .......................... 423/638, 566.2, 423/206.1, 206.2, 208, 225

[56] References Cited

U.S. PATENT DOCUMENTS

| | | | |
|---|---|---|---|
| 2,776,870 | 1/1957 | Fischer | 23/2 |
| 4,112,051 | 9/1978 | Sartori et al. | 423/223 |
| 4,624,838 | 11/1986 | Pan et al. | 423/226 |
| 4,647,397 | 3/1987 | Starkston et al. | 252/189 |
| 4,775,519 | 10/1988 | Yit Nieh | 423/226 |
| 4,978,512 | 12/1990 | Dillon | 423/226 |
| 5,128,049 | 7/1992 | Gatlin | 210/752 |

FOREIGN PATENT DOCUMENTS 2103645  2/1983  United Kingdom.

*Primary Examiner*—Richard L. Raymond
*Attorney, Agent, or Firm*—Panitch Schwarze Jacobs & Nadel

[57] ABSTRACT

A method is provided for the regeneration of a scavenging compound that has been reacted with hydrogen sulfide. Regeneration is accomplished through the use of calcium oxides and sodium hydroxide. Sodium sulfide is recovered from the regeneration process in a commercially useful form. Calcium oxides are also regenerated in the process, allowing for minimal or no chemical waste.

21 Claims, No Drawings

METHODS FOR RECOVERING SODIUM SULFIDES FROM A SULFUR SCAVENGING REACTION

CROSS-REFERENCE TO RELATED APPLICATION

This application is a continuation-in-part of U.S. patent application Ser. No. 08/026,891, filed Mar. 5, 1993, now allowed.

FIELD OF THE INVENTION

The present invention relates to methodology for removing hydrogen sulfide from liquid and gaseous streams. More particularly, the invention is directed to the preparation of calcium sulfides by the reaction of calcium oxides with either hydrogen sulfide or the reaction product(s) of hydrogen sulfide and nitrogen-containing scavenger compounds, and the subsequent reaction of the calcium sulfides with sodium hydroxide to regenerate the calcium oxides and prepare sodium sulfides.

DEFINITIONS

As used herein, the term "sodium sulfide" refers to the compound represented by the structural formula $Na_2S$, and the plural term "sodium sulfides" refers to one or more of the various sulfides of sodium, including sodium sulfide, ($Na_2S$), sodium hydrosulfide (NaSH), and their various hydrated forms.

As used herein, the term "calcium oxide" refers to the compound represented by the structural formula CaO, and the plural term "calcium oxides" refers to one or more of the various oxides of calcium, including calcium oxide (CaO), calcium hydroxide ($Ca(OH)_2$), and their various hydrated forms.

As used herein, the term "calcium sulfide" refers to the compound represented by the structural formula CaS, and the plural term "calcium sulfides" refers to one or more of the various sulfides of calcium, including calcium sulfide (CaS), calcium hydrosulfide ($Ca(SH)_2$), and their various hydrated forms.

As used herein, the term "scavenging compound(s)" means any nitrogen-containing chemical compound that, upon contact with a liquid or gaseous stream comprising hydrogen sulfide, will react with the hydrogen sulfide so as to substantially reduce the concentration of hydrogen sulfide in the stream.

As used herein, the term "hetero compound" includes a scavenging compound that has been at least partially reacted with hydrogen sulfide, so as to either provide a complex between hydrogen sulfide and a nitrogen atom of the scavenging compound, or to effect removal of at least one nitrogen from the scavenging compound with replacement thereof with a sulfur atom of a hydrogen sulfide molecule.

BACKGROUND OF THE INVENTION

Hydrogen sulfide is a toxic, corrosive and malodorous compound. It may be found in a variety of liquid and gaseous media, such as natural gas, petroleum, refinery gas streams, carbon dioxide, hydrogen, coal gas streams, gas streams from viscose rayon production, tars and asphalt, shale gas, coke oven gases, ammonia synthesis gas, rubber vulcanization streams, gases from sulfurization plants, turpentine production, pulp and paper mill effluent, sewage, brine drilling mud, landfills, phosphoric acid production gas streams and other industrial gas streams and effluents. It is also found in the tail gases and liquids of some hydrogen sulfide scrubbing processes such as Claus plants and amine scrubbing units.

In part because hydrogen sulfide is a highly toxic, corrosive and malodorous chemical, its release into the environment is strictly regulated by the Environmental Protection Agency, the Department of Environmental Resources, and other regulatory agencies throughout the world. The release of hydrogen sulfide is also of concern because it has been linked to the formation of acid rain.

Methods for removing hydrogen sulfide from gaseous and liquid media including the sources listed above, may generally be classified as either regenerative and non-regenerative. Regenerative methods typically employ sulfur-scavenging compounds, and have the desirable feature that the scavenging compounds can be recycled. The regeneration of the sulfur-scavenging compounds reduces the cost, both economically and environmentally, associated with the sulfur removal process. For example, regeneratable sulfur-scavenging compounds which have reacted with hydrogen sulfide need not be disposed of as waste, but can be recycled back to an active form. In a preferred regenerative process, the sulfur from the hydrogen sulfide is also recovered in a useful form.

Various amines and alkanolamines, which may be regenerated, have been used to remove acids, such as hydrogen sulfide, from gas streams. U.S. Pat. No. 2,776,870 discloses that aqueous amines and alkanolamines are useful for removing acids from a gaseous mixture. Hydrogen sulfide may be selectively removed from gas streams containing carbon dioxide by use of triethanolamine or methyldiethanolamine.

British Published Patent Specification No. 2103645 discloses that hydrogen sulfide and carbon dioxide may be removed from a gas mixture by contacting the mixture with a solvent comprising a tertiary amine and a physical absorbent. Suitable physical adsorbents include N-methylpyrrolidone and sulfolane.

U.S. Pat. No. 4,112,051 discloses a process for removing acidic gases from a gaseous mixture with an amine-solvent liquid absorbent comprising (1) an amine comprised of at least about 50 mole percent of a sterically hindered amine; and (2) a solvent for the amine mixture which is also a physical absorbent for the acid gases. Suitable sterically hindered amines include various piperidine compounds. Suitable solvents include sulfones, pyrrolidone and piperidine compounds, to name a few.

U.S. Pat. No. 4,978,512 discloses methods for reducing the levels of hydrogen sulfide and organic sulfides in a hydrocarbon stream by contacting the stream with a composition comprising the reaction products of a lower alkanolamine with a lower aldehyde. The reaction products include triazine and/or bisoxazolidine compounds.

U.S. Pat. No. 4,647,397 discloses a process and composition for removing hydrogen sulfide and similar sulfides from a gas stream. The gas stream is contacted with a substituted aromatic nitrile having an electron-attracting substituent on the aromatic ring, where the substituent has electron-attracting ability at least equal to that of halogen, and an organic tertiary amine, in an inert organic solvent, such as N-methyl-2-pyrrolidone. The spent contacting solution may be regenerated by heating the solution above the decomposition temperature of the reaction products to separate the sulfides from the liquid phase absorbent solution.

U.S. Pat. No. 4,775,519 discloses a continuous process for removing acid gas components from a gas stream by counter-currently contacting the stream with an aqueous solution of a mixture of N-methyldiethanolamine (MDEA) with imidazole or a methyl substituted imidazole. The gas is de-absorbed from the MDEA and the imidazole by reducing the pressure and causing the gas to flash.

U.S. Pat. No. 4,624,838 discloses a process for removing acid gases from a gaseous stream by contacting the stream with an aqueous scrubbing solution containing a hetero nitrogen compound comprising either a five- or six- membered ring having a $pK_a$ no greater than about 8. Preferred hetero nitrogen compounds include imidazole and piperazine compounds.

U.S. Pat. No. 5,128,049 discloses a method for reducing the hydrogen sulfide content of hydrocarbon-containing fluids and aqueous solutions by injections of a dilute solution of a scavenging agent. Suitable scavenging agents include hexahydro-1,3,5-tris(2-hydroxyethyl)-s-triazine and various other compounds.

As described in our copending U.S. patent application Ser. No. 08/026,891, now U.S. Pat. No. 5,347,003, sodium sulfides may be formed from a hydrogen sulfide-containing stream and a sodium hydroxide solution. However, it has been observed that if any carbon dioxide is also present in the stream, some of the sodium sulfides may react with the carbon dioxide and regenerate hydrogen sulfide. Carbon dioxide presence in hydrogen sulfide containing streams is not uncommon, and presents significant problems for regenerative methods directed to scrubbing hydrogen sulfide from liquid and gaseous streams.

There is a need in the art for commercially viable methodology which can scavenge hydrogen sulfide from liquid and gaseous streams containing both hydrogen sulfide and carbon dioxide. An even greater benefit may be realized if the hydrogen sulfide is converted to a commercially useful form. The preparation of sulfur compounds in such form provides a further financial incentive for the scavenging of hydrogen sulfide and even further reduces the burden on waste disposal systems.

SUMMARY OF THE INVENTION

According to the present invention, there has been developed a method comprising (a) preparing calcium sulfides by reaction of calcium oxides with a sulfur-containing compound selected from the group consisting of hydrogen sulfide and a hetero compound, where the hetero compound is prepared by reaction of hydrogen sulfide with an amine compound; and (b) reacting the calcium sulfides from step (a) with sodium hydroxide so as to provide sodium sulfide and regenerate the calcium oxides.

According to a preferred embodiment, the calcium sulfides of step (a) are isolated from other reactants and products prior to their reaction with sodium hydroxide according to step (b). According to another embodiment, the conversion of calcium oxides to calcium sulfides is conducted in the presence of carbon dioxide. Suitable amine compounds have from 1 to about 200 nitrogen atoms, wherein each nitrogen atom is independently either a primary, secondary or tertiary amine. A preferred amine compound is selected from the group of N-C-N compounds, defined as having the formula (I):

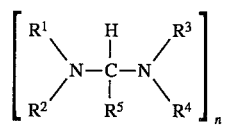

wherein n is an integer of 1 to 100, and each of $R^1$, $R^2$, $R^3$, $R^4$, and $R^5$ is independently selected from the group consisting of: (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; (iv) a substituted or unsubstituted polymeric chain; and (v) a direct bond to any other of $R^1$, $R^2$, $R^3$, $R^4$, and $R^5$.

Another aspect of the invention is a method for recovering sodium sulfides from a sulfur scavenging reaction mixture, comprising, reacting sodium hydroxide with calcium sulfides derived from a hydrogen sulfide scavenging process. In a preferred embodiment, the calcium sulfides are formed by either reacting calcium oxides with a hydrogen sulfide-containing stream, or as a product of a reaction between calcium oxides and a hetero compound, where the hetero compound is formed by reaction of an amine-containing scavenging compound with hydrogen sulfide. A preferred hetereo compound is derived from reacting an N-C-N compound of formula (I), above, with hydrogen sulfide.

The sodium hydroxide used in the inventive method is preferably in solution, with a concentration of about 10% to about 77% by weight of solvent; wherein the solvent is either water, alcohol or mixtures thereof. White liquor is a preferred source of sodium hydroxide.

According to another aspect of the invention, the sodium sulfide as prepared by any of the above methods is introduced into a wood pulping process to prepare pulp. Thus, the sodium sulfide can be added to the green liquor, a slaker or a causticiser, so as to participate in the pulping process.

Preferably, about 0.5 to about 8 molar equivalents of calcium oxides are reacted per molar equivalent of hetero compound. The calcium oxides may be added to the hetero compound in the presence of a hydrogen sulfide-containing stream. Alternatively, the calcium oxides are added to the hetero compound in the substantial absence of a hydrogen sulfide containing stream. In either case, the conversion of calcium oxides to calcium sulfides may take place in the presence of carbon dioxide.

DESCRIPTION OF THE PREFERRED EMBODIMENTS

The inventive method acts to regenerate calcium oxides after they have been converted to calcium sulfides according to a hydrogen sulfide scavenging process. According to the invention, hydrogen sulfide may be scavenged from liquid and gaseous waste streams by contacting said streams with a hydrogen sulfide-reactive material. One such method for scavenging hydrogen sulfide employs amine compounds, and particularly N-C-N compounds, as described in our copending application, Ser. No. 08/026,891, now U.S. Pat. No. 5,347,003, the disclosure of which is herein incorporated by reference.

Amine compounds suitable for scavenging hydrogen sulfide from liquid and gaseous streams include compounds having 1 to 200 nitrogen atoms, and 0–3 hydroxyl groups, where each nitrogen atom is independently either a primary, secondary, or tertiary amine group. Exemplary, and non-limiting, amine compounds include methyldiethanolamine, bis(dibutylamino)methane, bis(di-2-hydroxyethylamino)methane, bis(morpholino)methane, 1,3,6,8-tricyclotetraaza[4,4,1,1$^{3,8}$]-dodecane, piperazine and piperidine. Ethylene amines, having the unit N-CH$_2$CH$_2$-N are included in the amine compounds of the invention, where an exemplary ethylene amine is diethylenetriamine. Diamine compounds having the "N-C-N" unit, and referred to herein as "N-C-N compounds" are a preferred amine-containing scavenging compound according to the invention.

N-C-N compounds are defined as those compounds having the formula (I):

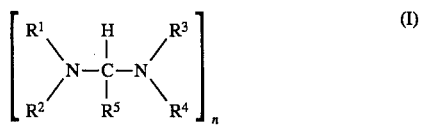

wherein n is an integer selected from within the range of 1 to 100, and each of $R^1$, $R_2$, $R^3$, $R_4$, and $R^5$ is independently selected from the group consisting of: (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; (iv) a substituted or unsubstituted polymeric chain; and (v) a direct bond to any other of $R^1$, $R^2$, $R^3$, $R^4$, and $R^5$.

In describing compounds of formula (I), it is convenient to give the name "N-C-N unit" to the structure shown within the square brackets. When n is greater than one, compounds of formula (I) have more than one N-C-N unit, such that at least two N-C-N units are adjacent to one another. When more than one N-C-N unit is present in a compound of formula (I), then adjacent units are joined together through at least one linkage formed from one of the groups $R^1$, $R^2$, $R^3$, $R^4$, or $R^5$ on a first N-C-N unit, wherein $R^1$, $R^2$, $R^3$, $R^4$, and $R^5$ are as defined above, and at least one of the groups $R^1$, $R^2$, $R^3$, $R^4$, and $R^5$ on a second adjacent N-C-N unit, wherein said $R^1$, $R^2$, $R^3$, $R^4$, or $R^5$ on the second N-C-N unit is a direct bond.

Examples of scavenging compounds having the N-C-N unit, which are useful in the initial scavenging step of the present method include various triazines, such as 1,3,5-tris(2-hydroxyethyl)hexahydro-s-triazine and trimethyl triazine, and bisoxazolidines, such as N,N'-methylene bisoxazolidine.

The amine-containing scavenger compounds, including the N-C-N compounds, after reacting with hydrogen sulfide, form product mixtures which are known herein as hetero compounds. Equation (I) illustrates the reaction products obtained when an exemplary N-C-N compound, a triazine derivative, reacts with hydrogen sulfide to yield a dithiazine and a primary amine complex. The primary amine complex could also be prepared upon direct reaction of hydrogen sulfide with a primary amine.

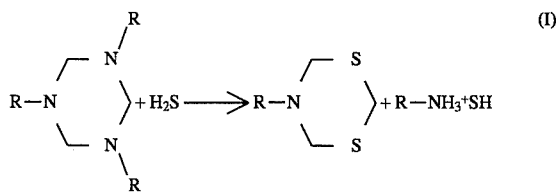

After reaction with hydrogen sulfide to provide hetero compound, the amine-containing scavenger compounds, including N-C-N compounds, can be regenerated by reacting the hetero compound(s) with calcium oxides. This reaction to regenerate N-C-N compounds is described in U.S. patent application Serial No. 08/026,891, now U.S. Pat. No. 5,347,003. The regeneration reaction may be accomplished by first removing the hetero compound from contact with the hydrogen sulfide-containing stream and then carrying out the reaction with calcium oxides. Alternatively, regeneration can be achieved by adding calcium oxides to the hetero compound while the hetero compound is still in contact with the hydrogen sulfide-containing stream. In the alternative case, an excess of calcium oxide will react with the hydrogen sulfide that is present in the stream. The products of these regeneration reactions are the N-C-N or other amine-containing scavenger compounds, in admixture with calcium sulfides. The calcium sulfides may be reacted so as to provide calcium oxides as described herein.

Generally, about 0.5 to about 8 molar equivalents of calcium oxides are mixed with one molar equivalent of hetero compound. Preferably, about 0.5 molar equivalents to about 4 molar equivalents of calcium oxide are used per molar equivalent of hetero compound and, more preferably, about 1 to about 2 molar equivalents of calcium oxides are used. Generally, if lower quantities of calcium oxides are used, some unregenerated hetero compound will remain in the solution. An excess of calcium oxides is not believed to detrimentally effect the reaction, although the presence of excess materials naturally incurs additional handling expense. If an excess of calcium oxides is used, a mixture of calcium oxides and calcium sulfides will be present in the product mixture.

In a preferred embodiment, the calcium sulfides are removed from the reaction system, i.e., separated from the other reactants and products present after the calcium oxides have been converted to calcium sulfides. This may be accomplished through settling, filtration, centrifugation, distillation, or any other means known in the art. When means other than distillation to dryness are used, it is preferred to follow separation of the calcium sulfides with a washing step to remove any residual scavenging compound. The rinse solution may then be returned to the scavenging system to minimize depletion of the scavenging compound through excess carryover into the calcium sulfide. In a preferred embodiment the washing step is carried out with water.

Yet another means according to the invention in which hydrogen sulfide may be scavenged from liquid and gaseous waste streams so as to provide calcium sulfides is to contact the stream directly with calcium oxides. Such direct contact converts the hydrogen sulfide and calcium oxides into calcium sulfides. The calcium sulfides may be converted back to calcium oxides according to the inventive methods described herein.

When hydrogen sulfide is present in a gaseous stream, the hydrogen sulfide-containing stream may be passed over a bed of calcium oxides, or bubbled through a slurry containing calcium oxides in a contact tower or bubble tower. When the hydrogen sulfide is present in an aqueous stream, the calcium oxides may be mixed with the stream to react with the hydrogen sulfide. The resultant calcium sulfides may be left in contact with the liquid, or may be removed by settling, filtration, centrifugation, evaporation, distillation, or other means known in the art.

In another aspect of the invention, calcium sulfides prepared as described above, are reacted with sodium hydroxide so as to provide calcium oxides. While being acted upon by sodium hydroxide, the calcium sulfides may be separated from other reactants and products, or may continue to be in admixture with other reactants and products, as present during the formation of the calcium sulfides.

For example, when calcium sulfides are formed during the regeneration of N-C-N compounds or other amine, the action of sodium hydroxide may take place in the presence of waste streams containing hydrogen sulfide, in the presence of unreacted N-C-N or other amine compounds, and/or in the presence of hetero compounds formed upon the reaction of the hydrogen sulfide-laden waste streams with N-C-N or other amine compounds. In addition, where the calcium sulfides are formed during direct reaction of calcium oxides with hydrogen sulfide-laden streams, the action of sodium hydroxide to regenerate calcium oxides from calcium sulfides may, but need not, occur in the presence of calcium oxides and/or hydrogen sulfide-laden waste streams.

The calcium sulfides are reacted with sodium hydroxide, preferably in solution form, to regenerate calcium oxides. The calcium sulfides are mixed with the sodium hydroxide solution for a period of time, and with sufficient agitation to effect the conversion of calcium sulfides to calcium oxides and of sodium hydroxide to sodium sulfides. Mixing for up to 4 hours is preferred with 1 to 3 hours being more preferred and 1–2 hours being most preferred. More time may be required if mixing is inadequate or absent. Additional mixing will not adversely effect the conversion of calcium sulfides to sodium sulfides and calcium oxides.

The sodium hydroxide solution is preferably at a concentration of 10% to 77% by weight in water or alcohol. A more preferred concentration of 25% to 60%, and a most preferred concentration of 40% to 55% may also be employed.

Upon completion of the reaction of calcium sulfides with sodium hydroxide, the solid calcium oxides so formed may be removed from the sodium sulfides-containing solution through settling, filtration, centrifugation, or any other means known in the art. It is preferred to follow separation of the calcium oxides with a washing step to remove any residual sodium sulfides. In a preferred embodiment, the washing step is carried out with water. Once removed, the calcium oxides may be utilized for the regeneration of a spent scavenging compound, or alternately further refined in a lime kiln.

The methods of the present invention are particularly useful for regenerating scavenging compounds in or near a kraft pulp mill or a sulfite pulp mill. In such cases, the calcium sulfides recovered from the regeneration of the scavenging compound are reacted with either caustic soda or white liquor (both of which comprise sodium hydroxide) present at the mill. The resultant slurry of sodium sulfides and calcium oxides are added to an appropriate point in the kraft or recovery processes, such as the green liquor, slaker or the caustisizer. A caustisizer is a piece of equipment present in a Kraft mill and used in the final step of a process to recover or regenerate white liquor, where said process takes black liquor to green liquor, and then green liquor to white liquor, as is well known in the art. Once present in this system, the sodium sulfides are returned to the pulping process in the regenerated white liquor, while the calcium oxides are recovered in the lime kiln or sold or used for other purposes. The paper mill realizes a particular benefit in such a process because it allows for the recovery of all of the sulfur scavenging reaction chemicals as well as the recovery of sodium sulfides that are necessary for the pulping process.

The following examples are set forth as a means of illustrating the present invention and are not to be construed as a limitation thereon.

Example 1

40.08 grams of a 45% by weight aqueous solution of 1,3,5-tri(2-hydroxyethyl)hexahydro-s-triazine was diluted with 55 grams of water. The resultant solution was placed in a gas sparging tube and reacted with approximately equal volumes of a mixture of 99.5% hydrogen sulfide and 25% carbon dioxide in argon until the solution was found to no longer absorb hydrogen sulfide. 10 grams of the spent solution was then reacted with 0.96 grams of calcium oxide in approximately 20 ml of water. The slurry was air agitated at 70° C. for six hours, during which time, no hydrogen sulfide was evolved. Analysis of the resultant reaction products indicated complete regeneration of the 1,3,5-tri(2-hydroxyethyl)hexahydro-s-triazine and the formation of calcium sulfide.

Example 2

Eleven grams of a 45% by weight aqueous solution of 1,3,5-tri(2-hydroxyethyl)hexahydro-s-triazine was diluted with 29 grams of water. The resultant solution was placed in a gas sparging tube and reacted with approximately equal volumes of a mixture of 99.5% hydrogen sulfide and 25% carbon dioxide in argon until the solution was found to no longer absorb hydrogen sulfide. The scavenging solution reacted with a total of 1.43 grams of hydrogen sulfide. 3.0 grams of calcium oxide was added to the sparging tube. The slurry was air agitated for one hour at room temperature. After one hour, the resultant calcium sulfides were filtered off and the regenerated scavenging solution was returned to the gas sparging tube and reacted with approximately equal volumes of a mixture of 99.5% hydrogen sulfide and 25% carbon dioxide in argon until the solution was found to no longer absorb hydrogen sulfide. The scavenging solution reacted with a total of 1.43 grams of hydrogen sulfide. 3.0 grams of calcium oxide was added to the sparging tube. The slurry was air agitated for one hour at room temperature. After one hour, the resultant calcium sulfides were filtered off and the regenerated scavenging solution was returned to the gas sparging tube and reacted with approximately equal volumes of a mixture of 99.5% hydrogen sulfide and 25% carbon dioxide in argon until the solution was found to no longer absorb hydrogen sulfide. The scavenging solution reacted with a total of 1.43 grams of hydrogen sulfide.

Example 3

Three grams of a mixture of solid calcium oxides and calcium sulfides, as recovered from the regeneration reaction of a scavenging compound was reacted with 15.05 grams of a 50% aqueous sodium hydroxide solution using vigorous stirring. A noticeable color change, indicating reaction, was observed after 2 minutes. The reaction was found to be essentially complete after two hours. After sitting overnight, a white solid was separated from the liquid phase by vacuum filtration. Both the solid and the liquid phases were analyzed for sulphur by X-Ray Fluorescence. The solid, calcium-containing phase was found to contain 0.00092 grams of sulfur (0.05% by weight). The liquid phase was found to contain 0.01869 grams of sulfur. 95.3 percent of the recovered sulfur had been converted to sodium sulfide in the aqueous phase.

Example 4

One thousand gallons of a 10% solution of 1,3,5-tri(2-hydroxyethyl)hexahydro-s-triazine is reacted with a kraft mill's hydrogen sulfide-containing stream in a contact tower until an increase in the amount of hydrogen sulfide passing through the contact tower is observed. The spent scavenging compound is drained from the contact tower and placed in a mixing vessel where it is reacted with 8100 pounds of calcium oxide; the resultant slurry is agitated for two hours. After two hours, the calcium sulfides which form are filtered from the slurry using a vacuum filter. The calcium sulfides on the filter are then washed with water to further remove residual scavenging compound and are returned to the contact tower along with the filtered, regenerated scavenging compound. The calcium sulfides are returned to the mixing vessel where they are reacted with 2,300 gallons of a 50% sodium hydroxide solution with agitation for two hours. After two hours, the resultant slurry is added to the caustisizer.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method comprising
   (a) preparing calcium sulfides by reaction of calcium oxides with a sulfur-containing hetero compound, where the hetero compound is prepared by reaction of hydrogen sulfide with an amine compound; and
   (b) reacting the calcium sulfides from step (a) with sodium hydroxide to produce sodium sulfides and regenerate the calcium oxides.

2. The method according to claim 1 wherein the calcium sulfides of step (a) are isolated from other reactants and products prior to their reaction with sodium hydroxide according to step (b).

3. The method according to claim 1 wherein the reaction of calcium oxides is conducted in the presence of carbon dioxide.

4. The method according to claim 1 wherein the amine compound is selected from the group consisting of molecules having from 1 to about 200 nitrogen atoms and 0–3 hydroxyl groups present in a molecule, wherein each nitrogen atom is independently either a primary, secondary or tertiary amine.

5. The method according to claim 4 wherein the amine compound is selected from the group consisting of hexylamine, heptylamine, octylamine, nonylamine, decylamine, piperazine, piperidine, ethanolamine, diethanolamine, methyl diethanolamine, N-CH$_2$CH$_2$-N compounds, triethanolamine and N-C-N compounds.

6. The method according to claim 5 wherein the N-C-N compound is represented by the formula (I):

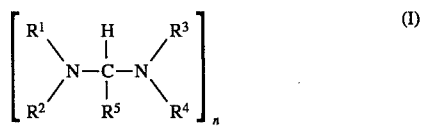

wherein n is an integer of 1 to 100, and each of R$^1$, R$_2$, R$^3$, R$^4$, and R$^5$ is independently selected from the group consisting of: (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; (iv) a substituted or unsubstituted polymeric chain; and (v) a direct bond to any other of R$^1$, R$^2$, R$^3$, R$^4$, and R$^5$.

7. The method according to claim 1 wherein about 0.5 to about 8 molar equivalents of calcium oxides are present to react with each molar equivalent of hetero compound.

8. The method according to claim 1 wherein the sodium hydroxide is present in a solvent, at a concentration of about 10% to about 77% (w/w), and the solvent is selected from the group consisting of water and alcohol.

9. A method for recovering sodium sulfides from a sulfur scavenging reaction mixture comprising, reacting sodium hydroxide with calcium sulfides formed as a product of a reaction between calcium oxides and a sulfur-containing hetero compound, where the hetero compound is formed by reaction of an amine-containing scavenging compound with hydrogen sulfide.

10. A method as in claim 9, wherein the calcium sulfides are formed as a product of a reaction between calcium oxides and a hetero compound, where the hetero compound is formed by reaction of an amine-containing scavenging compound with hydrogen sulfide.

11. A method as in claim 10, wherein the hetero compound is formed from a primary, secondary or tertiary amine.

12. A method as in claim 10, wherein the amine-containing scavenging compound is an N-C-N compound represented by the formula (I):

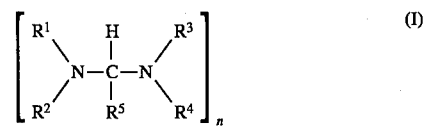

where n is an integer of 1 to 100. Each of R$^1$, R$^2$, R$^3$, R$^4$, and R$^5$ is independently selected from the group consisting of: (i) hydrogen; (ii) a substituted or unsubstituted, saturated or unsaturated, linear, branched or cyclic hydrocarbon chain of 1 to 20 carbons; (iii) a substituted or unsubstituted, saturated or unsaturated, linear, branched or cyclic hydrocarbon chain of 1 to 20 carbons comprising at least one heteroatom selected from the group consisting of nitrogen, oxygen, sulfur and halogen; (iv) a substituted or unsubstituted polymeric chain; and (v) a direct bond to any other of R$^1$, R$^2$, R$^3$, R$^4$, and R$^5$.

13. A method as in claim 12 wherein the N-C-N compound is 1,3,5-(2-hydroxyethyl)hexahydro-s-triazine.

14. A method as in claim 10 wherein about 0.5 to about 8 molar equivalents of calcium oxides are reacted per molar equivalent of hetero compound.

15. A method as in claim 10 wherein about 1 to about 2 molar equivalents of calcium oxides are reacted per molar equivalent of hetero compound.

16. A method as in claim 9, wherein the sodium hydroxide is in a solution with a concentration of about 10% to about 77% by weight of solvent; wherein said solvent is selected from the group consisting of water and alcohol.

17. A method as in claim 9, wherein the sodium hydroxide is in a solution with a concentration of about 40% to about 55% by weight of solvent; wherein said solvent is selected from the group consisting of water and alcohol.

18. A method as in claim 9, wherein the sodium hydroxide is in the form of white liquor.

19. A method as in claim 9, wherein the calcium oxides are added to the hetero compound in the presence of a hydrogen sulfide containing stream.

20. A method as in claim 9 wherein the calcium oxides are added to the hetero compound in the substantial absence of a hydrogen sulfide containing stream.

21. A method as in claim 9 wherein the calcium sulfides are derived in the presence of carbon dioxide from a hydrogen sulfide scavenging process.

* * * * *